US006977155B2

(12) United States Patent
Lahiri et al.

(10) Patent No.: US 6,977,155 B2
(45) Date of Patent: Dec. 20, 2005

(54) ARRAYS OF BIOLOGICAL MEMBRANES AND METHODS AND USE THEREOF

(75) Inventors: Joydeep Lahiri, Painted Post, NY (US); Ye Fang, Painted Post, NY (US); Steven J. Jonas, Bloomfield Hills, MI (US); Peter J. Kalal, Corning, NY (US); Wei Wang, Pittsford, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/854,786

(22) Filed: May 14, 2001

(65) Prior Publication Data

US 2002/0019015 A1 Feb. 14, 2002

Related U.S. Application Data

(60) Provisional application No. 60/224,135, filed on Aug. 10, 2000.

(51) Int. Cl.$^7$ .................. G01N 33/53; G01N 33/552

(52) U.S. Cl. ................. 435/7.2; 435/4; 435/7.1; 435/288.3; 436/518; 436/527

(58) Field of Search ................. 435/7.1, 288, 291, 435/287.1, 287.2, 877, 817, 174, 176, 177, 178, 179, 181, 288.3, 7.2; 436/525, 526, 527, 501, 806; 422/82.01, 82.02, 82.03; 204/400, 403; 530/816

(56) References Cited

U.S. PATENT DOCUMENTS

| 4,933,285 | A | * | 6/1990 | Patton ..................... 435/176 |
|---|---|---|---|---|
| 5,677,196 | A | | 10/1997 | Herron et al. ............. 436/518 |
| 5,756,355 | A | * | 5/1998 | Lang et al. ................ 204/194 |
| 5,919,576 | A | * | 7/1999 | Hui et al. .................. 428/545 |
| 6,117,990 | A | | 9/2000 | Bonini et al. |
| 6,383,778 | B1 | | 5/2002 | Zuker et al. |
| 6,451,543 | B1 | | 9/2002 | Kochendoerfer et al. |
| 6,503,452 | B1 | | 1/2003 | Boxer et al. |

FOREIGN PATENT DOCUMENTS

| WO | WO 96/26432 | | 8/1996 | |
|---|---|---|---|---|
| WO | WO 98/16830 | * | 4/1998 | .......... G01N/33/53 |
| WO | WO 98/23948 | | 6/1998 | |
| WO | WO 99/35289 | | 7/1999 | |
| WO | WO 00/04389 | | 1/2000 | |
| WO | WO 01/01142 | | 1/2001 | |
| WO | WO 01/20330 | | 3/2001 | |
| WO | WO 01/26800 | | 4/2001 | |
| WO | WO 01/88182 | | 11/2001 | |

OTHER PUBLICATIONS

Plant, Anne L., Supported Hybrid Bilayer Membranes as Rugged Cell Membrane Mimics, 1999, Langmuir, 15(15), 5128–5135.*

Bieri et al., "Micropatterned immobilization of a G protein-coupled receptor and direct detction of G protein activation", Nov. 17, 1999, Nature Biotechnology, 17(11):1105–1108.*
Paul S. Cremer et al., "Creating Spatially Addressed Arrays of Planar Supported Fluid Phospholipid Membranes", J. Am. Chem. Soc. 1999, vol. 121, No. 35, pp. 8130–8131.
Paul S. Cremer et al., "Formation and Spreading of Lipid Bilayers on Planar Glass Supports", J. Phys. Chem. B., 1999, vol. 103, No. 13, pp. 2554–2559.
Christoph Bieri et al., "Micropatterned Immobilization of a G Protein–Coupled Receptor and Direct Detection of G Protein Activation", Nature Biotechnology, vol. 17, Nov. 1999, pp. 1105–1108.
Jennifer S. Hovis et al., "Patterning Barriers to Lateral Diffusion in Supported Lipid Bilayer Membranes by Blotting and Stamping", Langmuir, vol. 16, No. 3, 2000, pp. 894–897.
Emili et al, Large–Scale functional analysis using peptide or protein arrays, Nature Biotechnology, vol. 18, Apr. 2000 393–396.
H. Lang et al., "A New Class of Thiolipids for the Attachment of Lipid Bilayers on Gold Surfaces", Langmuir 1994, vol. 10, pp. 197–210.
B. Raguse et al., "Tethered Lipid Bilayer Membranes: Formation and Ionic Reservoir Characterization", Langmuir 1998, vol. 14, pp. 648–659.
J.T. Groves et al., "Micropatterning Fluid Lipid Bilayers on Solid Supports", Science vol. 275, Jan. 31, 1997, pp. 651–653.
J.T. Groves et al., "Substrate–Membrane Interactions: Mechanisms for Imposing Patterns on a Fluid Bilayer Membrane", Langmuir, 1998, vol. 14, pp. 3347–3350.
B. Raguse et al., "Tethered Lipid Bilayer Membranes: Formation and Ionic Reservoir Characterization", Langmuir, 1998, pp. 648–659.
J.M. Stadel et al., "Orphan G Protein–Coupled Receptors: A Neglected Opportunity for Pioneer Drug Discovery", TiPS, Nov. 1997, vol. 18, pp. 430–437.
G. MacBeath et al., "Printing Proteins as Microarrays for High Throughput Function Determination", Science, Sep. 8, 2000, vol. 289, pp. 1760–1763.

(Continued)

*Primary Examiner*—Padmashri Ponnaluri
*Assistant Examiner*—My-Chau T. Tran
(74) *Attorney, Agent, or Firm*—Thomas R. Beall; Scott S. Servilla; Kaplan Gilman Gibson & Dernier L.L.P

(57) ABSTRACT

The present invention overcomes the problems and disadvantages associated with prior art arrays by providing an array comprising a plurality of biological membrane microspots associated with a surface of a substrate that can be produced, used and stored, not in an aqueous environment, but in an environment exposed to air under ambient or controlled humidities. Preferably, the biological membrane microspots comprise a membrane bound protein. Most preferably, the membrane bound protein is a G-protein coupled receptor, an ion channel or a receptor tyrosine kinase.

11 Claims, 7 Drawing Sheets

OTHER PUBLICATIONS

J. Drews, "Drug Discovery: A Historical Perspective", Science, Mar. 17, 2000, vol. 287, pp. 1960–1964.

A.D. Howard et al., "Orphan G–Protein–Coupled Receptors and Natural Ligand Discovery", Trends in Pharmacological Sciences, Mar. 2001, vol. 22, No. 3, pp. 132–140.

O. Civelli et al., "Orphan Receptors, Novel Neuropeptides and Reverse Pharmaceutical Research", Brain Research 848, 1999, pp. 63–65.

V.V. Gurevich et al., "Agonist–Receptor–Arrestin, an Alternative Ternary Complex with High Agonist Affinity", The Journal of Biological Chemistry, Nov. 14, 1997, vol. 272, No. 46, pp. 28849–28852.

R.H. Oakley et al., "Differential Affinities of Visual Arrestin, βArrestin1, and βArrestin 1 for G Protein–Coupled Receptors Delineate Two Major: Classes of Receptors", The Journal of Biological Chemistry, Jun. 2, 2000, vol. 275, No. 22, pp. 17201–17210.

L.S. Barak et al., "A β–Arrestin/Green Fluorescent Protein Biosensor for Detecting G Protein–Coupled Receptor Activation", The Journal of Biological Chemistry, Oct. 31, 1997, vol. 272, No. 44, pp. 27497–27500.

A. Kovoor et al., "Targeted Construction of Phosphorylation–Independent β–Arrestin Mutants with Constitutive Activity in Cells", The Journal of Biological Chemistry, Mar. 12, 1999, vol. 274, No. 11, pp. 6831–6834.

J. Lahiri et al., "Method for Fabricating Supported Bilayer Lipid Membranes on Gold", Langmuir, 2000, vol. 16, pp. 7805–7810.

W.W. Shen et al., "Polymer–Supported Lipid Bilayers on Benzophenone–Modified Substrates", Biomacromolecules, 2001, vol. 2, pp. 70–79.

E. Sackmann, "Supported Membranes: Scientific and Practical Applications", Science, Jan. 5, 1996, vol. 271, pp. 43–48.

S.M. Nielsen et al., "Constitutive Activation of Tethered-Peptide/Corticotropin–Releasing Factor Receptor Chimeras", Proc. Natl. Acad. Sci., Aug. 30, 2000, vol. 97, No. 18, pp. 10277–10281.

S. Angers et al., Detection of $β_2$–Adrenergic Receptor Dimerization in Living Cells Using Bioluminescence Resonance Energy Transfer (BRET), Proc. Natl. Acad. Sci., Mar. 28, 2000, vol. 97, No. 7, pp. 3684–3689.

A.J. Morris et al., "Physiological Regulation of G–Protein-Linked Singaling", Physiological Reviews, Oct. 1999, vol. 79, No. 4, pp. 1373–1430.

* cited by examiner

Figure 5
(A)
[BT-neurotensin] (nM)
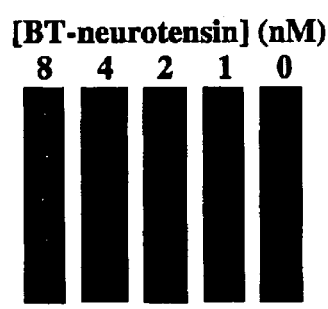
(B)
[cy5-antogonist D] (nM)
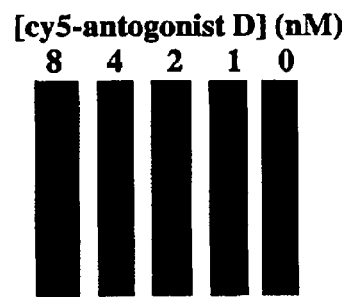

ARRAYS OF BIOLOGICAL MEMBRANES AND METHODS AND USE THEREOF

CLAIM OF PRIORITY

This Application claims priority of U.S. Provisional Application No. 60/224,135, filed on Aug. 10, 2000, the contents of which are incorporated by reference.

BACKGROUND OF THE INVENTION

DNA microarrays have become an extremely important bioanalytical tool (e.g. for analyzing gene-expression); protein microarray technology has, however, lagged behind. The fabrication of protein arrays is challenging because of difficulties associated with preserving the folded conformation of proteins in the immobilized state, and high amounts of non-specific binding to immobilized proteins. As a large fraction of drug targets are membrane bound proteins (e.g., G-protein coupled receptors, ion-channels, etc.), there is an impetus to develop tools for high-througput screening against membrane bound proteins. Membrane proteins maintain their folded conformation when associated with lipids; therefore, to create arrays of such proteins it is important to first develop surfaces that support the binding of membranes. Bilayer-lipid membranes adsorbed onto solid supports, referred to as supported bilayer-lipid membranes, can mimic the structural and functional role of biological membranes. See Sackmann, E. Science 1996, 271, 43–48; Bieri, C. et al., Nature Biotech, 1999, 17, 1105–1108; Groves, J. T. et al., Science 1997, 275, 651–653; Lang, H. et al., Langmuir 1994, 10, 197–210; Plant, A. L. et al., Langmuir 1999, 15, 5128–5135; and Raguse, B. et al., Langmuir 1998, 14, 648–659. These hybrid surfaces were developed to overcome the fragility of black lipid membranes while preserving aspects of lateral fluidity observed in native biological membranes.

Surfaces binding lipid membranes can be broadly classified into three categories:
(i) hydrophobic surfaces (e.g., self-assembled monolayers presenting terminal methyl groups) which support the adsorption of lipid monolayers are of limited utility as they cannot be used to incorporate membrane-spanning proteins (Plant, A. L., Langmuir 1999, 15, 5128–5135);
(ii) hydrophilic surfaces (e.g., glass surfaces) which bind bilayer-lipid membranes are also of limited utility as they can only be used to incorporate membrane-spanning proteins with extra-membrane domains that are less thicker than the layer of adsorbed water (~10° A) (Groves, J. T. et al., Science 1997, 275, 651–653; and Groves, J. T. et al., Langmuir 1998, 14, 3347–3350); and (iii) amphiphilic surfaces that contain hydrophobic and hydrophilic portions that bind bilayer-lipid membranes offer the potential for incorporating a wide variety of membrane-spanning proteins (Lang, H. et al., Langmuir 1994, 10, 197–210; Raguse, B. et al., Langmuir 1998, 14, 648–659; and Vanderah, D. J. et al., Materials Research Society Fall Meeting Abstracts, Boston, 1999).

Methods to create arrays of membranes would enable high-throughput screening of multiple targets against multiple drug-candidates. Arrays of membranes may be obtained by fabricating grids of titanium oxide on a glass substrate as titanium oxide resists the adsorption of lipids (Boxer, S. G. et al. Science 1997, 275, 651–653; and Boxer, S. G. et al. Langmuir 1998, 14, 3347–3350). Micropipeting techniques have been used to spatially address each corralled lipid-binding region (Cremer, P. S. et al., J. Am. Chem. Soc. 1999, 121, 8130–8131). However, these methods are cumbersome and require the fabrication of patterned surfaces. To make membrane arrays by printing membranes on unpatterned surfaces, it would be necessary to confine the membrane to the printed areas without lateral diffusion of the membrane molecules to the unprinted areas. Boxer et al. demonstrated that it was possible to pattern lipids on glass surfaces by microcontact printing using polydimethylsiloxane (PDMS) stamps "inked" with phosphatidylcholine ("PC"). They attributed the lateral confinement of the lipids to the stamped regions, to the self-limiting expansion of PC membranes to ~106% of the original printed areas (Hovis, J. et al., Langmuir 2000, 16, 894–897). The methods used by Boxer et al., however, have certain limitations. First, Boxer and co-workers carried out the stamping of lipids on surfaces immersed under water (Hovis 2000). Second; lipids adsorbed on the bare-glass substrates used by Boxer and co-workers spontaneously desorbed when drawn through an air-water interface (Cremer 1999). Cremer et al., propose in WO01/20330 the use of spatially addressed lipid bilayer arrays that remain submerged underwater to preserve the planar support structure. Such systems may not be practical for robust, high throughput, microarray based assays.

SUMMARY OF THE INVENTION

The present invention overcomes the problems and disadvantages associated with prior art arrays by providing an array comprising a plurality of biological membrane microspots associated with a surface of a substrate that can be produced, used and stored, not in an aqueous environment, but in an environment exposed to air under ambient or controlled humidities. Preferably, the biological membrane microspots comprise a membrane bound protein. Most preferably, the membrane bound protein is a G-protein coupled receptor, an ion channel or a receptor tyrosine kinase.

The substrate for use in the array of the present invention can comprise glass, silicon, metal or polymeric materials. The substrate can be configured as a chip, a slide or a microplate.

In certain embodiments, the surface of the substrate is coated. Preferably, the coating is a material that enhances the affinity of the biological membrane microspot for the substrate. Most preferred coating material confers a contact angle ranging from about 15° to 80°.

The coating material can be a silane, thiol, or a polymer. Preferably, when the material is a thiol, the substrate comprises a gold-coated surface. Preferably, the thiol comprises hydrophobic and hydrophilic moieties. Most preferably, the thiol is a thioalkyl compound.

Preferably, when the coating material is a silane, the substrate comprises glass. Preferably, the silane presents terminal polar moieties including, for example, hydroxyl, carboxyl, phosphate, sulfonate, or amino groups. A most preferred silane coating material γ-aminopropyl-silane.

In an alternative embodiment, the coating material is a derivatized monolayer (or several monolayers) having covalently bonded linker moieties. Most preferably, the monolayer comprises a thioalkyl compound or a silane compound.

Preferably, the thioalkyl compound is selected from the group consisting of a thioalkyl acid, thioalkyl alcohol, thioalkyl amine, and halogen containing thioalkyl compound. Most preferably, the thioalkyl compound is a thioalkyl acid, for example, 16-mercaptohexadecanoic acid.

Preferably, the silane compound is selected from the group consisting of a silyl anhydride, silyl acid, silyl amine, silyl alcohol, vinyl silane or silyl acrylate.

The bonded linker moiety can comprises a straight or branched $C_{10}$–$C_{25}$ alkyl, alkynyl, alkenyl, aryl, araalkyl, heteroalkyl, heteroalkynyl, heteroalkenyl, heteroaryl, heteroaraalkyl molecule that in turn includes:

(i) a terminal functional group capable of reacting with the derivatized monolayer;
(ii) a hydrophilic spacer region; and
(iii) a hydrophobic membrane adhering region.

The preferably, the terminal functional group is selected from the group consisting of a carboxylic acid, halogen, amine, thiol, alkene, acrylate, anhydride, ester, acid halide, isocyanate, hydrazine, maleimide and hydroxyl group. The hydrophilic spacer region preferably comprises n oxyethylene groups, wherein n=2 to 25. The membrane adhering region preferably comprises a straight or branched chain $C_{10}$–$C_{25}$ hydrophobic tail.

In further alternative embodiments the surface is nanoporous.

The present invention also provides a method for producing an array of biological membranes. The method comprises the steps of providing a substrate having a surface; providing a solution of a biological membrane (as used herein a "solution of a biological membrane" also includes a suspension of a biological membrane);immersing the tip of a pin into the solution; removing the tip from the solution to provide a solution adhered to the tip; contacting the solution with the surface to thereby transfer the solution from the tip to the surface; and repeating the contacting step a plurality of times (at least twice) to provide biological membrane microspots patterned in an array on the surface. Typically, the surface of the substrate is exposed to air under ambient or controlled humidities when the tip of the pin contacts the substrate.

In a preferred embodiment, the solution comprises a protein. Preferably, the solution comprises a membrane bound protein. Most preferably, the membrane bound protein is a G-protein coupled receptor (GPCR), an ion channel or a receptor tyrosine kinase. In certain embodiments, the protein contains a mutation, e.g. a point mutation. In other embodiments, the solution comprises multiple proteins.

In an alternative embodiment, the method includes the additional step of contacting the microspot with a solution comprising a protein.

The present invention further provides for detecting a binding event between a probe array and target compounds. The method comprises contacting a solution comprising the target compound with an array of probe biological membrane microspots associated with a surface of a substrate, and detecting a binding event between at least one or more of the probe microspots with one or more of the constituents of the target. Preferably, at least one of the constituents of the target is labeled and the detection step comprises detecting the presence of the label. The detection of the label is preferably carried out by imaging based on the radioactivity, fluorescence, phosphorescence, chemiluminescence, or resonance light scattering emanating from the bound target. The substrate can be washed to remove unbound target prior to the detection step.

In an alternative embodiment, the array of microspots is incubated with labeled cognate target, and an unlabeled target compound and the binding event between the unlabeled target compound and the probe is determined by measuring a decrease in the signal of the label due to competition between the cognate labeled target and the unlabeled target compound for the probe. Preferably, the labeled cognate target is incubated with the array before incubation with the unlabeled target. In other embodiments, the target is unlabeled and binding event is determined by a change in physical properties at the interface or by mass spectroscopy. Preferably, the change in physical properties at the interface is a change in refractive index or electrical impedence.

Biosensors and diagnostic devices that comprise the arrays of the invention are also contemplated by the present invention.

DESCRIPTION OF THE DRAWINGS

The patent or application file contains at least one page of drawings executed in color. Copies of this patent or patent application publication with color drawings will be provided by the U.S. Patent and Trademark Office upon request and payment of the necessary fee.

In FIG. 2(A) the image corresponds to an array that was stored for 7 days at 4° C. in a container saturated with water vapor. In FIG. 2(B) the images correspond to arrays that were stored for 1,6, and 14 days in a dessicator at 4° C.

FIG. 3(A) fluorescence images of microarrays of DMP/DPPC (1:4) lipids doped with FITC-DHPE (2%) on GAPS slides that were subject to repeated immersions in buffer and withdrawn through air-water interfaces. (I) Fluorescence image of the lipid array immersed in buffer. (II) Fluorescence image of the array immersed in buffer after being withdrawn five times through an air-water interface. (III) Fluorescence image of the same array immersed in buffer after being withdrawn five more times through an air-water interface. (IV) Fluorescence image of the array in air after drying. (V) Fluorescence image of the same array under buffer after reimmersion. FIG. 3(B) fluorescence images of microarrays of egg PC (1:4) lipids doped with FITC-DHPE (2%) on GAPS slides that were subject to repeated immersions in buffer and withdrawn through air-water interfaces, as described above for (I)–(V). The data were collected using a ScanArray 5000 scanner. The buffer was used was 50 mM sodium phosphate, pH 7.5.

FIG. 4(A) fluorescence image of an array incubated with binding buffer only; this image serves as a negative control. FIG. 4(B) fluorescence image of a second array incubated with a solution of BT-NT (1 nM). FIG. 4(C) fluorescence image of an array incubated with a solution of BT-NT (1 nM) and CGP12177 (1 $\mu$M). FIG. 4(D) fluorescence image of an array incubated with a solution of BT-NT (1 nM) and SCH23390 (1 $\mu$M). FIG. 4(E) fluorescence image of an array incubated with a solution of BT-NT (1 nM) and neurotensin (1 $\mu$M). CGP12177 and SCH23390 are ligands that are known not to bind to NTR1 receptors; neurotensin is the cognate ligand for NTR1.

FIGS. 5(A) and 5(B) show fluorescent images of arrays of the present invention. FIG. 5(A) fluorescence images of 1×5 arrays of microspots of NTR1 incubated in solutions containing different concentrations of BT-neurotensin, as indicated in the figure. FIG. 5(B) fluorescence images of 1×5 arrays of microspots of the galanin receptor incubated in solutions containing different concentrations of cy5-labeled antagonist D, as indicated in the figure. The binding buffer was 50 mM Tris-HCl, 10 mM $MgCl_2$, 2 mM EDTA, 0.1% BSA, at pH 7.4.

DETAILED DESCRIPTION OF THE INVENTION

Biological membrane arrays, as well as methods for their preparation and use, are provided. In the arrays of the present invention, a plurality of biological membrane probe spots are stably associated with the surface of a solid support. The arrays of the present invention find particular use in identification of ligands for membrane bound proteins, such as G-protein coupled receptors. Additionally, the arrays of the present invention offer tremendous possibilities for high-throughput screening of multiple membrane bound targets against multiple drug-candidates, thereby greatly accelerating the process of drug discovery. In further describing the subject invention, the arrays themselves are first discussed, followed by a description of methods for their preparation. Next, a review of representative applications in which the subject arrays may be employed is provided.

It is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Arrays of the Present Invention

Figure 1:
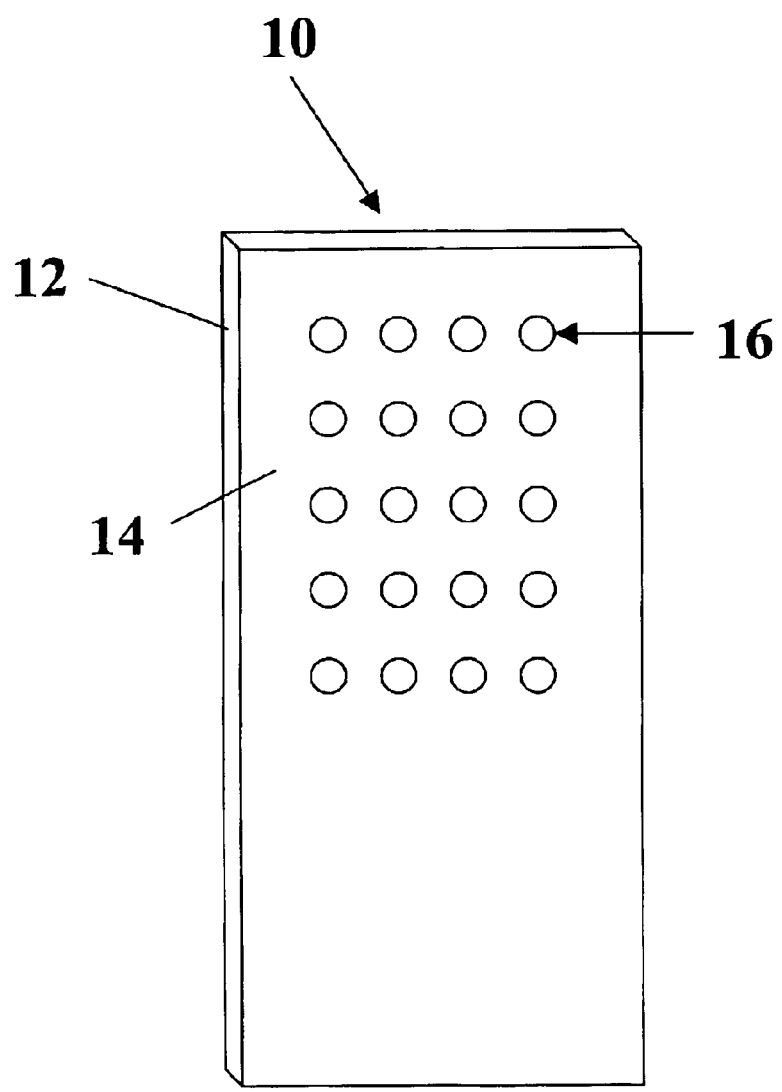
FIG. 1 shows a top view of an array of the present invention.

As illustrated in FIG. 1, the array (10) of the present invention includes a substrate (12) having a surface (14) having a plurality of biological membrane probe microspots (16) covering the surface (14). Each probe microspot on the array comprises a biological membrane of known composition and, in preferred embodiments, comprise a membrane bound protein. The microspot may comprise multiple different proteins. For example, two different proteins involved in a heterodimer pair can be included in one microspot. The probe microspots on the array may be any convenient shape, but will typically be circular, elliptoid, oval, annular, or some other analogously curved shape, where the shape may, in certain embodiments, be a result of the particular method employed to produce the array. The density of the all of the microspots on the surface of the substrate, i.e. both probe spots and non-probe spots, e.g. calibration spots, control spots, etc., is at least about $5/cm^2$ and usually at least about $10/cm^2$ but does not exceed about $1000/cm^2$, and in many embodiments does not exceed about $500/cm^2$, where in certain preferred embodiments, the density does not exceed about $400/cm^2$, usually does not exceed about $300/cm^2$, and more usually does not exceed about $60/cm^2$. The microspots may be arranged in any convenient pattern across or over the surface of the array, such as in rows and columns so as to form a grid, in a circular pattern, and the like, where generally the pattern of spots will be present in the form of a grid across the surface of the solid support.

In the arrays of the present invention, the microspots are stably associated with the surface of a substrate. By "stably associated" is meant that the biological membranes of the spots maintain their position relative to the substrate under binding and washing conditions, e.g., the membrane remains adsorbed when drawn through an air-water interface. As such, the biological membranes which make up the spots can be non-covalently or covalently stably associated with the substrate surface. Examples of non-covalent association include non-specific adsorption, binding based on electrostatic (e.g. ion, ion pair interactions), hydrophobic interactions, hydrogen bonding interactions, surface hydration forces and the like. Examples of covalent binding include covalent bonds formed between the spot biological membranes and a functional group present on the surface of the substrate, e.g. —$NH_2$, where the functional group may be naturally occurring or present as a member of an introduced coating material. In another example, histidine-tagged mutations of GPCRs or membrane proteins can bind to Ni-presenting surfaces through chelating bonds.

Typically, when the biological membrane microspot comprises a membrane bound protein, only one type of protein is included in each microspot of the array. However, in certain situations more than one type of protein is included in each microspot. For example, some GPCRs heterodimerize for their biological functions. (Angers, S. et al., *Proc. Natl. Acad. Sci. USA*, 2000, 97, 3684–3689.) In a preferred embodiment of the array, the protein included in the microspot differs from the protein included on a second microspot of the same array. In such an embodiment, a plurality of different proteins are present on separate microspots of the array. Typically the array comprises at least about ten different proteins. Preferably, the array comprises at least about 50 different proteins. More preferably, the array comprises at least about 100 different proteins. Alternative preferred arrays comprise more than about $10^3$ different proteins or more than about $10^4$ different proteins. The array may even optionally comprise more than about $10^5$ different proteins.

In one embodiment of the array, each of the microspots of the array comprises a different protein. For instance, an array comprising about 100 microspots could comprise about 100 different proteins. Likewise, an array of about 10,000 microspots could comprise about 10,000 different proteins. In an alternative embodiment, however, each different protein is included on more than one separate microspot on the array. For instance, each different protein may optionally be present on two to six different microspots. An array of the invention, therefore, may comprise about three-thousand microspots, but only comprise about one thousand different proteins since each different protein is present on three different microspots.

In a further alternative embodiment, the array comprises identical microspots or a series of identical microspots that in use are treated with a different analyte (target). For example, an array of the invention can include a "mini array" of 20 microspots, each microspot containing a different membrane bound protein, wherein the mini array is repeated 20 times as part of the larger array.

In another embodiment of the present invention, although the protein of one microspot is different from that of another, the proteins are related. In a preferred embodiment, the two different proteins are members of the same protein family. The different proteins on the invention array may be either functionally related or just suspected of being functionally related. In another embodiment of the invention array, however, the function of the immobilized proteins may be unknown. In this case, the different proteins on the different microspots of the array share a similarity in structure or sequence or are simply suspected of sharing a similarity in structure or sequence. Alternatively, the proteins may be fragments of different members of a protein family.

Substrate

The substrates of the subject arrays comprise at least one surface on which the pattern of probe spots is present, where the surface may be smooth or substantially planar, or have irregularities, such as depressions or elevations. The surface on which the pattern of spots is present may be modified with one or more different layers of compounds that serve to modify the properties of the surface in a desirable manner and will be discussed in more detail below. The surface may also be nano-porous.

The substrate may consist of a ceramic substance, a glass, a metal, a crystalline material, a plastic, a polymer or co-polymer, any combinations thereof, or a coating of one material on another. For example, but not limited to, (semi) noble metals such as gold or silver; glass materials such as soda glass, pyrex glass, vycor glass, quartz glass; metallic or non-metallic oxides; silicon, monoammonium phosphate, and other such crystalline materials; transition metals; plastics or polymers, including dendritic polymers, such as poly(vinyl chloride), poly(vinyl alcohol), poly(methyl methacrylate), poly(vinyl acetate-maleic anhydride), poly (dimethylsiloxane) monomethacrylate, polystyrenes, polypropylene, polyethyleneimine; copolymers such as poly (vinyl acetate-co-maleic anhydride), poly(styrene-co-maleic anhydride), poly(ethylene-co-acrylic acid) or the like.

The substrate may take a variety of configurations ranging from simple to complex, depending on the intended use of the array. Thus, the substrate could have an overall slide or plate configuration, such as a rectangular or disc configuration. In many embodiments, the substrate will have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.1 mm to 2 mm and more usually from about 0.2 to 1 mm.

Coating Material

An array of the present invention may optionally further comprise a coating material on a portion of the substrate comprising the probe microspots. Preferably the coating material enhances the affinity of the biological membrane microspot for the substrate. Most preferably, the coating material confers a contact angle ranging from about 15° to 80°.

In one embodiment, the coating material is a silane, thiol, or a polymer. Preferably, when the material is a thiol, the substrate comprises a gold-coated surface. Preferably, the thiol comprises hydrophobic and hydrophilic moieties. Most preferably, the thiol is a thioalkyl compound.

Preferably, when the coating material is a silane, the substrate comprises glass. Preferably, the silane presents terminal polar moieties including, for example, hydroxyl, carboxyl, phosphate, sulfonate, or amino groups. A most preferred silane coating material γ-aminopropyl-silane.

γ-aminopropyl-silane coated slides (CMT-GAPS™ glass slides) are available commercially from Corning Inc.

In an alternative embodiment, the coating material is a derivatized monolayer or multilayer having covalently bonded linker moieties. The monolayer coating, for example, comprising of long chain hydrocarbon moieties, may have for example, but not limited to, thiol (e.g., thioalkyl), disulfide or silane groups that produce a chemical or physicochemical bonding to the substrate. The attachment of the monolayer to the substrate may also be achieved by non-covalent interactions or by covalent reactions.

Preferably, the thiol is a thioalkyl compound and is selected from the group consisting of a thioalkyl acid, thioalkyl alcohol, thioalkyl amine, and halogen containing thioalkyl compound. Most preferably, the thioalkyl compound is a thioalkyl acid, for example, 16-mercaptohexadecanoic acid. Such compounds can be readily synthesized and/or purchased from commercial sources.

After attachment to the substrate the monolayer has at least one reactive functional group. Examples of reactive functional groups on the monolayer coating are, but not limited to, carboxyl, isocyanate, halogen, amine or hydroxyl groups. In one embodiment, these reactive functional groups on the monolayer coating may be activated by standard chemical techniques to corresponding activated functional groups on the monolayer coating (for example, conversion of carboxyl groups to anhydrides or acid halides, etc.). The activated functional groups of the monolayer coating on the substrate may be, but not limited to, anhydrides, N-hydroxysuccinimide esters or other common activated esters or acid halides, for covalent coupling to terminal amino groups of the linker compound. In another embodiment, the activated functional groups on the monolayer coating may be, but not limited to, anhydride derivatives for coupling with a terminal hydroxyl group of the linker compound; hydrazine derivatives for coupling onto oxidized sugar residues of the linker compound; or maleimide derivatives for covalent attachment to thiol groups of the linker compound. To produce a derivatized monolayer coating at least one terminal carboxyl group on the monolayer coating is first activated to an anhydride group and then reacted with a linker compound.

Alternatively, the reactive functional groups on the monolayer coating may be reacted with a linker compound having activated functional groups, for example, but not limited to, N-hydroxysuccinimide esters, acid halides, anhydrides, and isocyonates for covalent coupling to reactive amino groups on the monolayer coating.

The linker compound has one terminal functional group, a spacer region and a membrane adhering region. The terminal functional groups for reacting with the activated functional groups on the activated monolayer coating are for example, but not limited to, halogen, amino, hydroxyl, or thiol groups. Preferably, the terminal functional group is selected from the group consisting of a carboxylic acid, halogen, amine, thiol, alkene, acrylate, anhydride, ester, acid halide, isocyanate, hydrazine, maleimide and hydroxyl group.

The spacer region may consist of, but not limited to, oligo/poly ethers, oligo/poly peptides, oligo/poly amides, oligo/poly amines, oligo/poly esters, oligo/poly saccharides, polyols, multiple charged species or any other combinations thereof For example, but not limited to, oligomers of ethylene glycols, peptides, glycerol, ethanolamine, serine, inositol, etc., and is such that membranes freely adhere to the membrane adhering region of the linker moiety. The spacer region may be hydrophilic in nature. In one preferred embodiment, the spacer has n oxyethylene groups, where n is between 2 and 25. In the most preferred embodiment, the spacer has ten oxyethylene groups. In a preferred embodiment the membrane adhering region or "hydrophobic tail" of the linker compound is hydrophobic or amphiphilic with straight or branched chain alkyl, alkynyl, alkenyl, aryl, araalkyl, heteroalkyl, heteroalkynyl, heteroalkenyl, heteroaryl, or heteroaraalkyl. In a preferred embodiment, the membrane adhering region comprises of a $C_{10}$ to $C_{25}$ straight or branched chain alkyl or heteroalkyl hydrophobic tail. In the most preferred embodiment, the hydrophobic tail comprises a $C_{10}$ to $C_{20}$ straight or branched chain alkyl fragment.

In another embodiment, the linker compound has a terminal functional group on one end, a spacer, a linker/membrane adhering region and a hydrophilic group on another end. The hydrophilic group at one end of the linker compound may be a single group or a straight or branched chain of multiple hydrophilic groups. For example, but not limited to, a single hydroxyl group or a chain of multiple ethylene glycol units.

Biological Membranes

In accordance with the present invention, a "biological membrane" as referred to in the present invention comprises a membrane which may be synthetic or naturally occurring, for example, but not limited to, vesicles, liposomes, monolayer lipid membranes, bilayer-lipid membranes, membranes incorporated with receptors, whole or part of cell membranes, or liposomes containing re-folded proteins, or detergent micelles containing re-folded proteins, or the like. Membranes suitable for use with the present invention are amphiphilic molecules, for example, but not limited to, phospholipids, sphingomyelins, cholesterol or their derivatives. In a preferred embodiment, the membrane includes a membrane-protein. Such membrane proteins include, for example, integral membrane proteins, peripheral membrane proteins and receptors (e.g., G protein-coupled receptors, ion-channel receptors, tyrosine kinase-linked receptors, cytokine receptors, and receptors with intrinsic enzymatic activity). In another embodiment, the membrane may be bilayer-lipid membranes incorporated with, but not limited to, ionophores (for example, but not limited to, valinomycin, nonactin, methyl monesin, coronands, cryptands or their derivatives), ion-channels (for example, but not limited to, protein ionophores, etc.) or synthetic or naturally occurring analytes, for example, but not limited to, antibody, enzyme, lectin, dye, chelating agent and the like.

Proteins

The proteins incorporated on the array may be produced by any of the variety of means known to those of ordinary skill in the art. In preparation for incorporation on the arrays of the present invention, the protein may be obtained from natural sources or optionally be overexpressed using recombinant DNA methods. Proteins include, for example, GPCRs (e.g. the aderenergic receptor, angiotensin receptor, cholecystokinin receptor, muscarinic acetylcholine receptor, neurotensin receptor, galanin receptor, dopamine receptor, opioid receptor, erotonin receptor, somatostatin receptor, etc), ion-channels (nicotinic acetylcholine receptor, sodium and potassium channels, etc), receptor tyrosine kinases, receptors for growth factors and hormones (epidermal growth factor (EGF) receptor), and other membrane-bound proteins. Mutants or modifications of such proteins may also be used. For example, some single or multiple point mutations of GPCRs retain function and may be involved in disease. (See, Stadel, et al., Trends in Pharmocological Review, 1997, 18, 430–437.)

Additionally, as discussed above, modifications include histidine tagging of a GPCR at the c-terminus. Such modified protein can be attached to the substrate surface in a specific orientation e.g., the intracellular domain of the GPCR facing the substrate. Moreover, the proteins can also (or independently) be modified to include an agonist (or peptide) attached at the N-terminus. GPCRs modified in such a way can be constitutively activated (Nielsen, S. M. et al., *Proc. Natl. Acad. Sci. USA*, 2000, 97, 10277–10281).

Preparation of the Arrays

The arrays of the present invention are prepared using micropauerning techniques. Such techniques are well known in the art. In a preferred method of preparation, the tip of a probe (also referred to as a "pin") is immersed into a solution of biological membrane. The tip is removed from the solution to provide solution adhered to the tip. The lipid solution is contacted with the surface of a substrate to thereby transfer the solution from the tip to the surface.

A "pin" as used in the invention may be of any shape, size, and dimension. For example, the pin printing process may involve ring shaped pins, square pins, or point pins, etc. In another embodiment, the direct contact printing may involve single pin-printing or multiple pin printing, i.e. a single pin printing method involving a source plate or multiple pin-printing using a laid out array of multiple pins patterned in any format.

The printing apparatus may include a print head, plate, substrate handling unit, XY or XYZ positioning stage, environmental control, instrument control software, sample tracking software, etc. For example, a quill pin-printer sold by Cartesian Technologies, Inc.

A typographical probe array having a matrix of probes aligned such that each probe from the matrix fits into a corresponding source well, e.g., a well from a microtiter plate, is preferably used to form a high density array.

Uses of the Arrays

The present invention also provides for methods of using the biological membrane array. The arrays of the present invention are particularly suited for the use in drug development, medical diagnostics, proteomics and biosensors.

The sample which is delivered to the array is typically a fluid.

A wide range of detection methods is applicable to the methods of the invention. As desired, detection may be either quantitative, semiquantitative, or qualitative. The invention array can be interfaced with optical detection methods such as absorption in the visible or infrared range, chemoluminescence, and fluorescence (including lifetime, polarization, fluorescence correlation spectroscopy (FCS), and fluorescence-resonance energy transfer (FRET)). Furthermore, other modes of detection such as those based on optical waveguides (PCT Publication WO96/26432 and U.S. Pat. No. 5,677,196), surface plasmon resonance, surface charge sensors, and surface force sensors are compatible with many embodiments of the invention.

The assays used on these arrays may be direct, noncompetitive assays or indirect, competitive assays. In the noncompetitive method, the affinity for binding sites on the probe is determined directly. In this method, the proteins in the microspots are directly exposed to the analyte ("the target"). The analyte may be labeled or unlabeled. If the analyte is labeled, the methods of detection would include fluorescence, luminescence, radioactivity, etc. If the analyte is unlabeled, the detection of binding would be based on a change in some physical property at the probe surface. This physical property could be refractive index, or electrical impedance. The detection of binding of unlabeled targets could also be carried out by mass spectroscopy. In the competitive method, binding-site occupancy is determined indirectly. In this method, the proteins of the array are exposed to a solution containing a cognate labeled ligand for the probe array and an unlabled target. The labeled cognate ligand and the unlabled target compete for the binding sites on the probe protein microspots. The affinity of the target for the probe microspot relative to the cognate ligand is determined by the decrease in the amount of binding of the cognate labeled ligand. The detection of binding of the target can also be carried out using sandwich assays in which after the initial binding, the array is incubated with a second solution containing molecules such as labeled antibodies that have an affinity for the bound target, and the amount of binding of the target is determined based on the amount of binding of the labeled antibodies to the probe-target complex.

Another aspect of the invention provides for a method for screening a plurality of proteins for their ability to bind a particular component of a target sample. This method comprises delivering the sample to an array of the invention comprising the proteins to be screened and detecting, either directly or indirectly, for the presence or amount of particular component retained at each microspot. In a preferred embodiment, the method further comprises the intermediate step of washing the array to remove any unbound or nonspecifically bound components of the sample from the array before the detection step. In another embodiment, the method further comprises the additional step of further characterizing the particular component retained on at least one microspot.

In another embodiment of the invention, a method of assaying for protein-protein binding interactions is provided which comprises the following steps: first, delivering a sample comprising at least one protein to be assayed for binding to the array of the invention; and then detecting, either directly, or indirectly, for the presence or amount of the protein from the sample that is retained at each microspot.

Another embodiment of the invention provides a method of assaying in parallel for the presence of a plurality of analytes in a sample which can react with one or more of the proteins on the array. This method comprises delivering the sample to the array and detecting for the interaction of the analyte with the protein at each microspot.

In still another embodiment of the invention, a method of assaying in parallel for the presence of a plurality of analytes in a sample which can bind one or more of the proteins on the array comprises delivering the fluid sample to the array and detecting, either directly or indirectly, for the presence or amount of analyte retained at each microspot. In a preferred embodiment, the method further comprises the step of washing the array to remove any unbound or non-specifically bound components of the sample from the array.

The array may be used in a diagnostic manner when the plurality of analytes being assayed are indicative of a disease condition or the presence of a pathogen in an organism. In such embodiments, the sample which is delivered to the array will then typically be derived from a body fluid or a cellular extract from the organism.

The array may be used for drug screening when a potential drug candidate is screened directly for its ability to bind or otherwise interact with a plurality of proteins on the array. Alternatively, a plurality of potential drug candidates may be screened in parallel for their ability to bind or otherwise interact with one or more proteins on the array. The drug screening process may optionally involve assaying for the interaction, such as binding, of at least one analyte or component of a sample with one or more proteins on an array, both in the presence and absence of the potential drug candidate. This allows for the potential drug candidate to be tested for its ability to act as an inhibitor of the interaction or interactions originally being assayed.

In general, delivery of solutions containing proteins to be bound by the proteins of the array may optionally be preceded, followed, or accompanied by delivery of a blocking solution. A blocking solution contains protein or another moiety which will adhere to sites of non-specific binding on the array. For instance, solutions of bovine serum albumin or milk may be used as blocking solutions.

In the following, the invention is illustrated by non-limiting examples which describe the invention.

EXAMPLES

Materials

Membrane preparations of human β-adrenergic receptor subtype I (β1) and dopamine receptor subtype I (D1) were purchased from Biosignal Packard (Montreal, Canada). These receptor-associated membranes came suspended in a buffer solution containing 10 mM Tris-HCl, pH 7.4 and 10% glycerol. Human cloned neurotensin receptor subtype 1 (NT1R) and BODIPY-TMR-neurotensin (BT-NT) were purchased from Perkin Elmer Life Science (Boston, Mass.) and were received as membrane associated suspensions in a buffer solution containing 10 mM Tris-HCl (pH 7.4) and 10% sucrose. BODIPY-TMR-CGP12177 (BT-CGP) and BODIPY-FL-SCH23390 (BF-SCH) were purchased from Molecular Probes (Eugene, OR). CGP12177 and SCH23390 were purchased from Tocris Cookson, Inc (Ballwin, MO). Neurotensin was purchased from Sigma Chemical Co. (St. Louis, MO). Corning CMT-GAPS slides were used as received. Brij 76 derivatized gold-coated substrates were prepared as described previously. The fluorescently labeled ("hot") ligands and neurotensin were dissolved in DMSO and stored at −20° C. Before use, the ligand solution was diluted using a binding buffer consisting of 50 mM Tris-HCl, 2 mM EDTA, 1 mM $MgCl_2$, pH 7.4 and 0.1% bovine serum albumin (BSA).

1,2-dilauroyl-sn-glycero-2-phosphocholine (DLPC), L-α-dimyristoylphosphatidylcholine (DMPC), L-α-dipalmitoylphosphatidycholine (DPPC), and egg phosphatidylcholine (egg PC), were purchased from Avanti Polar Lipids (Alabaster, Ala.). FITC-1,2-dihexadecanoul-sn-glycero-3-phosphoethanolamine (FITC-DHPE) and Texas Red-1,2-dihexadecanoul-sn-glycero-3-phosphoethanolamine (TR-DHPE) were purchased from Molecular Probes Inc.

GPCR and Lipid Printing

Multiple arrays of GPCRs or lipids were printed on each slide (Corning CMT-GAPS slides) using a robotic pin printer (Model PS 5000, Cartesian Technologies Inc.) equipped with quill pins (Telechem). Each 3×3 or 5×5 element array was separated from its neighboring array by at least 6 mm. Membrane preparations containing GPCRs were used for printing as received from the manufacturer without further purification or dilution. After printing the arrays were incubated in a humid chamber at room temperature for one hour, and then used for ligand binding experiments. For longer term storage, the arrays were stored in a dessicator at 4° C.

Ligand Binding

Each array on a given slide was incubated for one hour with 10 μL of a buffered solution (50 mM Tris-HCl, 2 mM EDTA, 1 mM $MgCl_2$, pH 7.4, 0.1% BSA) containing ligand. After incubation, the solutions were carefully removed using a pipette tip attached to a vacuum pump. The slides were rinsed briefly with water and dried under a stream of nitrogen. The slides were imaged in a GenPix 4000 scanner (Axon Instruments, Foster City, Calif.).

Fluorescence Recovery After Photobleaching (FRAP)

Small unilamellar vesicles (SUVs) of 1,2-dilauroyl-sn-glycero-2-phosphocholine (DLPC) mixed with 2% (mol) Texas Red DHPE were generated by sonicating a suspension of the lipids (1 mg/ml) in buffer; these vesicles were then incubated with the substrate. After extensive and careful washing, supported lipid membranes were formed on these surfaces. FRAP experiments were carried out on these supported lipid membranes on bare glass and GAPS slides using an Olympus AX70 epifluorescence microscope equipped with a CCD detector (Princeton Instruments).

Results and Discussion

Fabrication and Storage of GPCR Arrays

Arrays of GPCRs were fabricated by conventional robotic pin printing, using a quill-pin printer as described in the Experimental Section. Boxer and co-workers have described the importance of transferring membranes onto the solid-support under water; we were, however, concerned that the lipid solution wetted onto the pin would partially dissociate from the pin under water and cause cross-contamination during printing. Moreover, slide racks in commercially available printers are not set up for printing under water. The ability to use off-the-shelf printing equipment for fabricating membrane-protein arrays is an important step towards the widespread fabrication and development of these arrays for bioanalytical applications.

Figure 2:
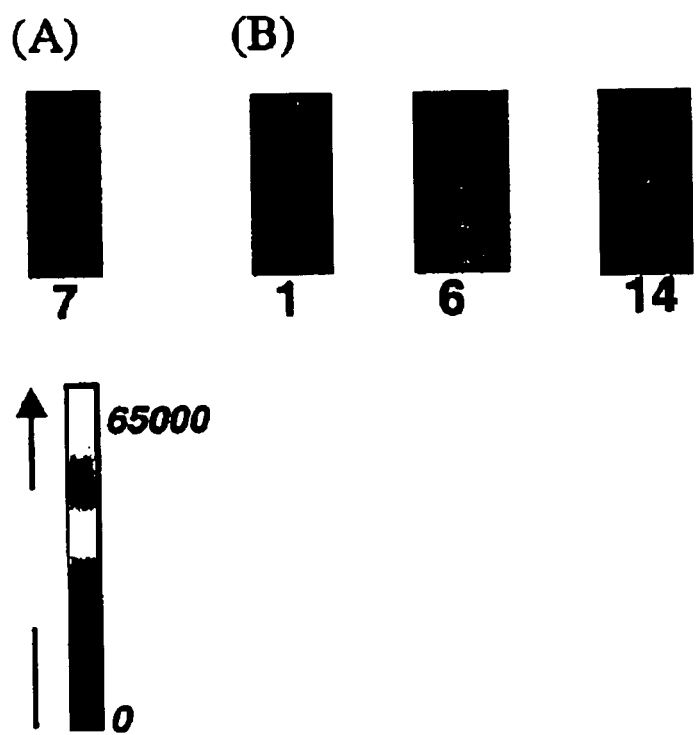
FIGS. 2(A) and 2(B) show fluorescence images of 1×5 arrays of microspots of the β-adrenergic receptor (subtype 1) incubated with solutions of BT-TMR CGP12177 (5 nM).

In order to investigate the stability of printed GPCR proteins, arrays of the adrenergic β1 receptor were printed as targets. We first investigated the storage of these arrays under high-humidity at various temperatures (room temp to −80° C.). These high-humidity conditions were chosen because there was a significant body of literature that suggested the importance of an aqueous environment for maintaining the structure of the membrane-protein complex. (Macbeath G., Schreiber, S. L. Science 2000, 289, 1760–1761; Cremer, P. S. Boxer, S. G. J. Phys. Chem. B 1999, 103, 2554–2559). The functional stability of the arrays was evaluated in binding assays using fluorescently labeled cognate ligands and inhibitors using protocols described in Experimental. No ligand binding to the arrays was observed after storage for a week (FIG. 2A). Therefore, we decided to test the stability of these arrays under desiccation. We felt that desiccation would reduce possible protease-induced degradation; we also found out that flash-plates with immobilized GPCRs when stored desiccated at 4° C. were stable for up to 3 months. Under the new conditions, the slides with printed GPCR arrays were air dried at room temp for a couple of hours, put into slide holders under nitrogen, and stored in desiccators at 4° C. in the dark. Our observations indicate that, over a 2-week period, the adrenergic β1 receptors retained their ligand-binding affinity (FIG. 2B). These stability experiments are a significant feasibility milestone for the manufacture of GPCR arrays.

Mechanical Stability of Membrane Arrays on GAPS Substrates

Figure 3:
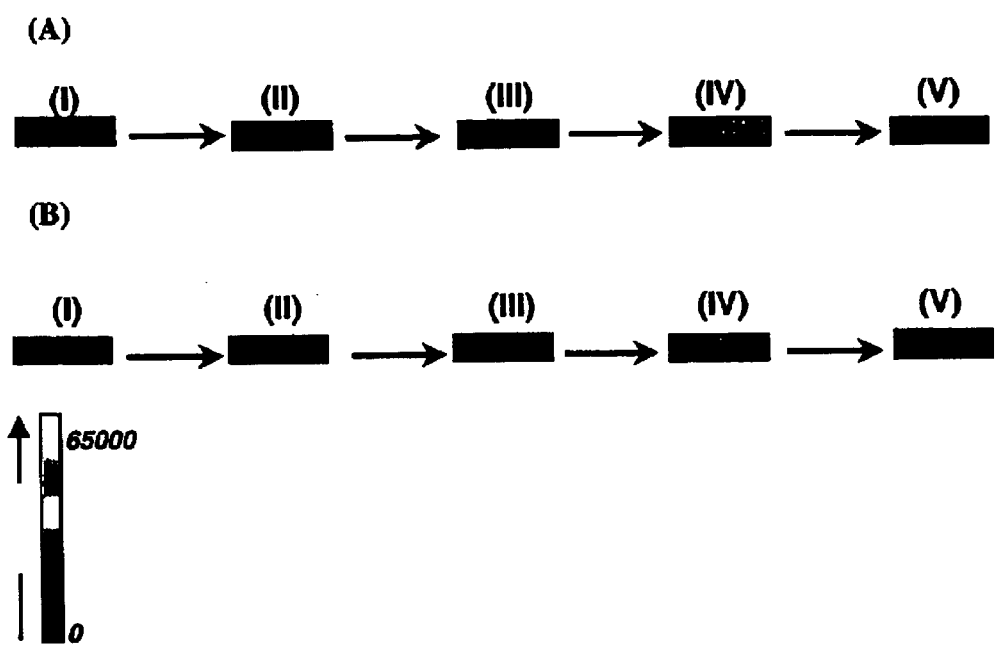
FIGS. 3(A) and 3(B) are fluorescent images of microarrays of the present invention.

We were interested in the development of robust binding assays for membrane-protein arrays. Boxer and co-workers have reported that lipids adsorbed onto bare-glass substrates spontaneously desorbed when drawn through an air-water interface (Cremer and Boxer, 1999). We felt that this behavior was a limitation to the use of membrane-protein arrays for bioassays, which often requires protocols in which the slides are withdrawn from solution (e.g. during washes by successive immersions). We therefore investigated surfaces that supported the adsorption of mechanically stable supported membranes; our criterion for stability was that the supported membrane would remain adsorbed when withdrawn through an air-water interface. Among the several surfaces tested, the CMT-GAPS surfaces offered the most stable supported lipids. FIG. 3A shows fluorescence images of arrays of supported membranes consisting of DPPC/DMPC doped with fluorescein-DHPE immersed in buffer that were withdrawn through an air-water interface, immersed in water, dried, and again immersed under water. We do not see any decrease in the fluorescence intensities of these lipid microspots through these successive immersions and withdrawals; these observations indicate that the bound lipids are stable. FIG. 3B shows data on lipids consisting of egg PC; arrays of these lipids are also stable when subject to successive immersions and withdrawals. At room temperature, DMPC/DPPC lipids are in the gel-phase, whereas egg-PC is in the fluid phase. These experiments demonstrate that supported lipid arrays are mechanically robust on GAPS-coated substrates, independent of whether they are in the gel or fluid phase.

We were also interested in determining whether the lipids adsorbed on GAPS substrates had long-range lateral fluidity. This fluidity is an important characteristic of native biological membranes, and is a property that is considered to be physiologically significant (e.g. for processes such ligand induced receptor dimerization at surfaces). Although it is not clear whether this fluidity is required for ligand screening experiments on supported biological membranes, we nevertheless wanted to investigate whether the high mechanical stability of the supported lipids described above necessarily implied that the lipids were not laterally mobile. We made vesicles from fluorescently labeled DLPC lipids and formed supported lipids on the GAPS substrates by vesicle fusion. Using a fluorescence microscope, we were able to observe fluorescence recovery of a photobleached spot on the supported lipid in a FRAP experiment. A comparative experiment with DLPC vesicles on bare-glass suggested that the recovery was much slower on the GAPS substrate; there was also a certain fraction of lipids on the GAPS substrate that did not "recover", suggesting that a certain fraction of the supported membrane was immobile. Nevertheless, these experiments suggest there is some lateral fluidity associated with the supported lipids on the GAPS substrates. Our observations on the GAPS substrates are in agreement with the lower and limited mobility of supported membranes on polymer cushions reported by Shen et al (William W Shen, Steven G. Boxer, Wolfgang Knoll, Curtis W. Frank; Biomacromolecules 2001, vol 2, pp 70–79).

Biospecific Binding to GPCR Arrays

Figure 4:
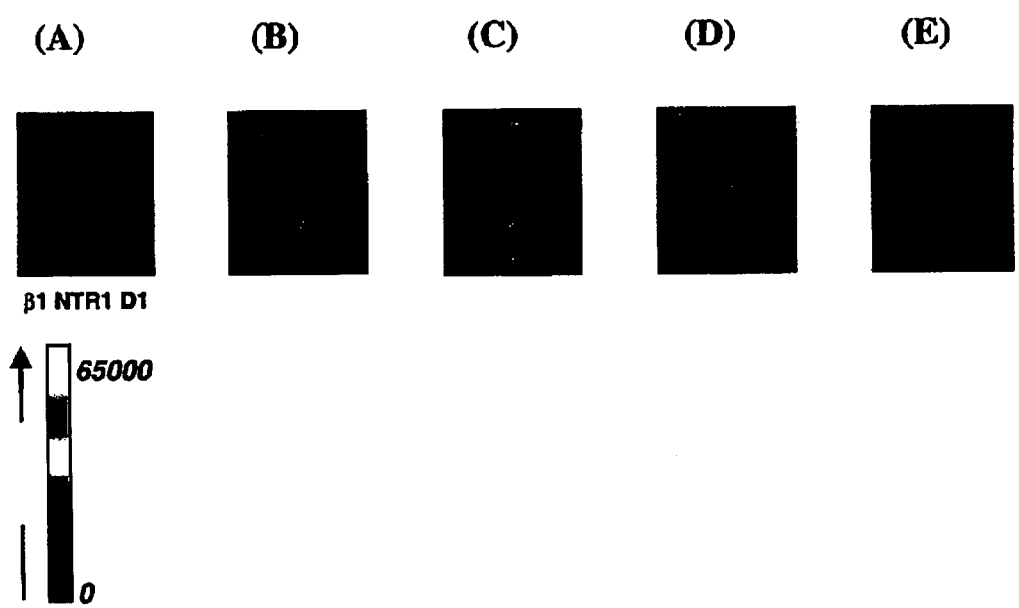
FIGS. 4(A)–4(E) show fluorescence images of GPCR arrays, in which each array contains three columns and each column consists of five replicate microspots. Each column of microspots corresponds to a different GPCR. From left to right, these receptors are the β-adrenergic receptor subtype I (β1), the neurotensin receptor subtype I (NTR1), and the dopamine receptor subtype I (D1).
Figure 6:
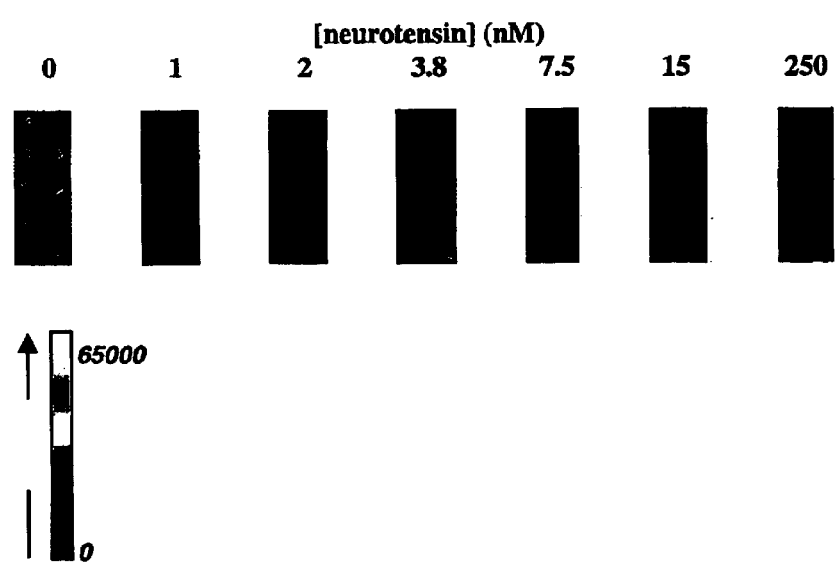
FIG. 6 shows fluorescence images of NTR1 receptor arrays incubated in solutions containing BT-neurotensin at fixed concentration (2 nM) and unlabeled neurotensin at different concentrations in the binding buffer (FIG. 6(A)).
Figure 7:
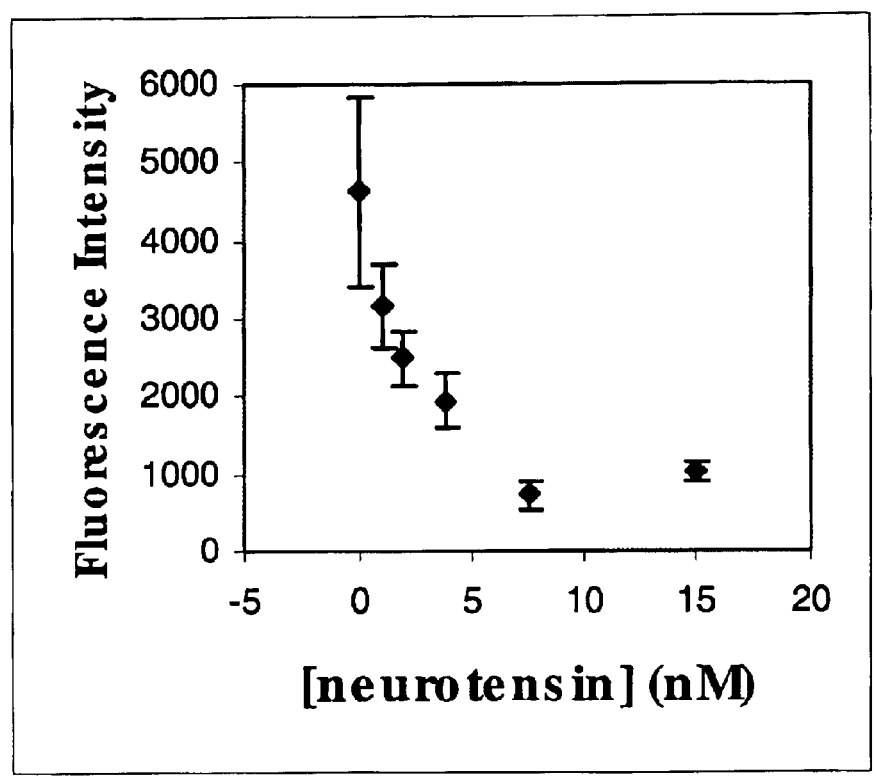
FIG. 7 shows the concentrations of neurotensin used in the example illustrated in FIG. 6.

Arrays of GPCRs were fabricated by using a quill-pin printer, as described above. The arrays were then incubated with their fluorescently labeled cognate ligands in direct or competition assays. FIG. 4 shows fluorescence false-color images of five separate arrays printed on a single CMT-GAPS slide; each individual array contains three columns containing 5 replicate spots; each column represents a different GPCR protein. These proteins, from left to right, are the adrenergic receptor (β1), the neurotensin receptor (NTR1) and the dopamine (D1) receptor, respectively. The first array (FIG. 4A) was incubated with the binding buffer only. As expected, no fluorescence is observed. The second array (FIG. 4B) was incubated with a solution containing fluorescently labeled neurotensin (BT-NT, 1 nM). The image shows that only the array corresponding to NTR1 shows a strong fluorescence signal; this observation suggests that the binding of BT-NT to NTR1 is selective. The specificity of the interaction was further demonstrated by incubating the arrays with solutions containing BT-NT (1 nM) and either CGP12177 (1 µM) (FIG. 4C), SCH 23390 (1 µM) (FIG. 4D), or neurotensin (1 µM) (FIG. 4E). Relative to FIG. 4B, there is no significant decrease in the intensities of spots corresponding to NTR1 in FIGS. 4C and 4D. CGP 12177 and SCH 23390 do not bind to NTR1; hence, their addition to the binding solution should not inhibit the interaction of BT-NT with NTR1, in agreement with our observations. Neurotensin is the cognate ligand for NTR1, hence, it competes for binding sites on the NTR1 array. In FIG. 4E, the array was incubated with a solution that contained neurotensin in 1000-fold excess over BT-NT; at these ratios, the neurotensin is expected to completely inhibit the binding of BT-NT to NTR1. We do not observe any signal corresponding to the NTR1 array; hence, neurotensin is able to specifically inhibit binding to NTR1. These experiments demonstrate that assays to test the binding of ligands and inhibitors are feasible using GPCR arrays.

Dose Dependent Binding

We have investigated the response of the printed GPCR arrays to cognate ligands at different concentrations. FIG. 5A shows fluorescence images of arrays of the neurotensin receptor treated with BT-NT; the data shows that there an increase in the fluorescence intensity of the arrays when treated with higher concentrations of the fluorescently labeled ligand. For the binding of BT-neurotensin to NTR1 arrays, the limit of detection was ~0.1–0.2 nM BT-NT. These results suggest that the dynamic range of GPCR arrays utilizing fluorescently labeled ligands is ~2 logs for this system. FIG. 5B shows data for the binding of cy5-labeled antagonist D to arrays of the galanin receptor—the images show that the fluorescence intensity of the microspots are dependent on the concentration of the ligand.

The inhibition of binding of the fluorescent ligands to the array is dependent on the relative concentrations of the inhibitor and the labeled ligands, and their respective dissociation ($K_d$) and inhibition constants ($K_i$). FIG. 6 shows fluorescence images of NTR1 arrays incubated with solutions containing BT-NT (2 nM) and different concentrations of neurotensin (0–250 nM). The data shows that there is a decrease in the fluorescence as the concentration of neurotensin is increased. A plot of the fluorescence intensities versus concentration is shown in FIG. 7; based on this plot, we estimate that the inhibition constant ($K_i$) ~2.5 nM. This value is consistent with the reported value of $K_i$ (2 nM) for neurotensin obtained from fluorescence polarization experiments. These experiments demonstrate that it is possible to obtain estimates of binding constants of ligands and inhibitors using GPCR arrays.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

The references cited throughout the specification including those set forth below are incorporated herein by reference.

1. Malbon, C. C. and Morris, A. J. (1999). "Physiological regulation of G protein-linked signaling." *Physiol. Rev.* 79, 1373–1430.
2. Drews, J. (2000). "Drug discovery: a historical perspective". *Science* 287, 1960–1963.
3. Howard, A. D., McAllister, G., Feighner, S. D., Liu, Q., Nargund, R. P., Van der Ploeg, L. H. T. and Patchett, A. A. (2001) "Orphan G-protein coupled receptors and natural ligand discovery". *Trends in Pharmaco. Sci.* 22, 132–140.
4. Stadel, J. M., Wilson, S. and Bergsma, D. J. (1997). "Orphan G protein-coupled receptors: a neglected opportunity for pioneer drug discovery." *TiPS* 18, 430–437.
5. Civelli, O., Reinscheid, R. K., Nothacker, H.-P. (1999). "Orphan receptors, novel neuropeptides and reverse pharmaceutical research". *Brain Res.* 848, 63–65.
6. Gurevich, V. V., Pals-Rylaarsdam, R., Benovic, J. L., Hosey, M. M. and Onorato, J. J. (1997). "Agonist-receptor-arrestin, an alternative ternary complex with high agonist affinity." *J. Biol. Chem.* 272, 28849.
7. Oakley, R. H., Laporte, S. A., Holt, J. A., Caron, M. G., Barak, L. S. (2000) "Differential affinities of visual arrestin, β-arrestin1, and β-arrestin2 for G protein-coupled receptors delineate two major classes of receptors." *J. Biol. Chem.* 275, 17201–17210.
8. Barak, L. S., Ferguson, S. S. G., Zhang, J. and Caron, M. G. (1997). "A β-arrestin/green fluorescent protein biosensor for detecting G protein-coupled receptor activation.' *J. Biol. Chem.* 272, 27497–27500.
9. Kovoor, A., Celver, J., Abdryashitov, R., Chavkin, C., Gurevich, V. V. (1999). "Targeted construction of phosphorylation-independent β-arrestin mutants with constitutive activity in cells." *J. Biol. Chem.* 274, 6831–6834.
10. Lahiri, J., Kalal, P., Frutos, A. G., Jonas, S. J. and Schaeffler, R. (2000). "Method for fabricating supported bilayer lipid membranes on gold". *Langmuir* 16, 7805–7812.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. An array comprising a plurality of biological membrane microspots comprising G-protein coupled receptor stably associated with a surface of a glass substrate, the surface of the substrate comprising a γ-aminopronyl-silane coating.

2. The array of claim 1, wherein the biological membrane microspots retain their ability to bind to a ligand when stored in air.

3. The array of claim 1, wherein the substrate is configured as a chip, a slide or a microplate.

4. The array of claim 1 wherein the material confers a contact angle ranging from about 150 to 80°.

5. The array of claim 1, wherein the surface is nanoporous.

6. An array comprising a plurality of biological membrane microspots comprising G-receptor protein associated with the surface of a substrate, said substrate comprising glass, wherein the surface of the substrate is coated with γ aminopropyl-silane such that the array is capable of being produced, used, or stored in an environment exposed to air under ambient humidity.

7. The array of claim 6, wherein the biological membrane microspots retain their ability to bind to a ligand when stored in air.

8. The array of claim 6, wherein the substrate is configured as a chip, a slide or a microplate.

9. The array of claim 6, wherein the material confers a contact angle ranging from about 15° to 80°.

10. The array of claim 6, wherein the surface is nanoporous.

11. An array comprising a plurality of biological membrane microspots stably associated with a surface of a glass substrate, the membrane microspots having the ability to bind to a ligand after exposure to air under ambient humidity, wherein the surface is coated with γ-aminopropylsilane and the biological membrane microspots comprise a G-protein coupled receptor.

* * * * *

UNITED STATES PATENT AND TRADEMARK OFFICE
CERTIFICATE OF CORRECTION

PATENT NO. : 6,977,155 B2
APPLICATION NO. : 09/854786
DATED : December 20, 2005
INVENTOR(S) : Lahiri et al.

Page 1 of 1

It is certified that error appears in the above-identified patent and that said Letters Patent is hereby corrected as shown below:

col. 16, line 51

"contact angle ranging from about 150 to 80°." Should read
"contact angle ranging from about 15° to 80°."

Signed and Sealed this

Twenty-ninth Day of August, 2006

JON W. DUDAS
*Director of the United States Patent and Trademark Office*